(12) United States Patent
Hodges

(10) Patent No.: US 9,985,374 B2
(45) Date of Patent: May 29, 2018

(54) COMPLIANT IMPLANTABLE CONNECTOR AND METHODS OF USE AND MANUFACTURE

(71) Applicant: TC1 LLC, St. Paul, MN (US)

(72) Inventor: William V. Hodges, Tracy, CA (US)

(73) Assignee: TC1 LLC, St. Paul, MN (US)

( * ) Notice: Subject to any disclaimer, the term of this patent is extended or adjusted under 35 U.S.C. 154(b) by 0 days. days.

(21) Appl. No.: 15/588,470

(22) Filed: May 5, 2017

(65) Prior Publication Data
US 2017/0324185 A1    Nov. 9, 2017

Related U.S. Application Data

(60) Provisional application No. 62/332,987, filed on May 6, 2016.

(51) Int. Cl.
| | |
|---|---|
| *H01R 13/70* | (2006.01) |
| *H01R 13/193* | (2006.01) |
| *H01R 13/22* | (2006.01) |
| *H01R 43/26* | (2006.01) |

(Continued)

(52) U.S. Cl.
CPC ......... *H01R 13/193* (2013.01); *A61M 1/1008* (2014.02); *H01R 13/22* (2013.01); *H01R 13/5224* (2013.01); *H01R 43/26* (2013.01); *A61M 2205/8206* (2013.01); *A61M 2207/00* (2013.01); *H01R 2201/12* (2013.01)

(58) Field of Classification Search
CPC .. H01R 13/193; H01R 13/22; H01R 13/5224; H01R 43/26; H01R 2201/12
USPC ....................................................... 439/700
See application file for complete search history.

(56) References Cited

U.S. PATENT DOCUMENTS

| | | | |
|---|---|---|---|
| 4,591,222 A * | 5/1986 | Shaffer ................. | H01R 12/87 439/265 |
| 5,695,471 A | 12/1997 | Wampler | |
| 5,888,242 A | 3/1999 | Antaki et al. | |

(Continued)

OTHER PUBLICATIONS

The Importance of Contact Force. *Technical Tidbits* (Issue No. 6). [online] Brush Wellman Alloy Products, Jul. 2009 [retrieved on Aug. 10, 2017]. Retrieved from the Internet: <URL: https://materion.com/-/media/files/pdfs/alloy/newsletters/technical-tidbits/issue-no-06-the-importance-of-contact-force.pdf>, 2 pages.

*Primary Examiner* — Harshad C Patel
(74) *Attorney, Agent, or Firm* — Kilpatrick, Townsend & Stockton LLP (57) ABSTRACT

An implantable connector utilizing having improved electrical and mechanical properties is described herein. In one aspect, the implantable connector utilizes electrical contact pins fabricated from a corrosion resistant metal alloy, such as platinum-iridium, that engage longitudinally and include one or more urging members on a proximal portion of the pin so as to provide at least a desired contact force between conductively coupled pins. Such a configuration allows contact between contact pins to be maintained in applications where the connector may be subject to movement and further allows for reduced resistance so as to allow transmission of voltages and current associated with higher powered implanted devices. In some embodiments, the urging member is defined as a helical cut potion in one or both electrical contacts. Methods of use and manufacture of such connectors are also provided herein.

24 Claims, 8 Drawing Sheets

(51) Int. Cl.
*H01R 13/52* (2006.01)
*A61M 1/10* (2006.01)

(56) References Cited

U.S. PATENT DOCUMENTS

| | | | |
|---|---|---|---|
| 5,967,856 A * | 10/1999 | Meller | H01R 13/2428 439/700 |
| 6,006,135 A * | 12/1999 | Kast | A61N 1/3752 439/652 |
| 6,071,093 A | 6/2000 | Hart | |
| 6,083,059 A * | 7/2000 | Kuan | H01R 13/2428 439/482 |
| 6,116,862 A | 9/2000 | Rau et al. | |
| 6,186,665 B1 | 2/2001 | Maher et al. | |
| 6,234,772 B1 | 5/2001 | Wampler et al. | |
| 6,264,635 B1 | 7/2001 | Wampler et al. | |
| 6,688,861 B2 | 2/2004 | Wampler | |
| 6,991,595 B2 | 1/2006 | Burke et al. | |
| 7,040,935 B2 * | 5/2006 | Wei | H01R 13/2428 439/700 |
| 7,144,278 B2 * | 12/2006 | Le Gallic | H01R 13/2428 439/700 |
| 7,270,550 B1 * | 9/2007 | Peng | H01R 13/2428 439/66 |
| 7,575,439 B2 * | 8/2009 | Chen | H01R 13/2428 439/66 |
| 7,699,586 B2 | 4/2010 | LaRose et al. | |
| 7,942,677 B2 * | 5/2011 | Rikimaru | G01R 1/06722 439/66 |
| 7,976,271 B2 | 7/2011 | Larose et al. | |
| 7,997,854 B2 | 8/2011 | LaRose et al. | |
| 8,007,254 B2 | 8/2011 | Larose et al. | |
| 8,152,493 B2 | 4/2012 | Larose et al. | |
| 8,323,174 B2 | 12/2012 | Jeevanandam et al. | |
| 8,408,948 B2 * | 4/2013 | Selvitelli | A61B 5/0416 439/729 |
| 8,449,444 B2 | 5/2013 | Poirier | |
| 8,506,471 B2 | 8/2013 | Bourque | |
| 8,562,508 B2 | 10/2013 | Dague et al. | |
| 8,597,350 B2 | 12/2013 | Rudser et al. | |
| 8,652,024 B1 | 2/2014 | Yanai et al. | |
| 8,657,733 B2 | 2/2014 | Ayre et al. | |
| 8,668,473 B2 | 3/2014 | Larose et al. | |
| 8,682,431 B2 | 3/2014 | Callaway et al. | |
| 2005/0071001 A1 | 3/2005 | Jarvik | |
| 2007/0078293 A1 | 4/2007 | Shambaugh et al. | |
| 2008/0021394 A1 | 1/2008 | LaRose et al. | |
| 2009/0203957 A1 | 8/2009 | Larose et al. | |
| 2010/0331937 A1 * | 12/2010 | Foster | A61N 1/0573 607/116 |
| 2012/0046514 A1 | 2/2012 | Bourque | |
| 2012/0095281 A1 | 4/2012 | Reichenbach et al. | |
| 2012/0149229 A1 | 6/2012 | Kearsley et al. | |
| 2012/0158108 A1 * | 6/2012 | Foster | A61N 1/0573 607/119 |
| 2013/0096364 A1 | 4/2013 | Reichenbach et al. | |
| 2013/0121821 A1 | 5/2013 | Ozaki et al. | |
| 2013/0127253 A1 | 5/2013 | Stark et al. | |
| 2013/0170970 A1 | 7/2013 | Ozaki et al. | |
| 2013/0225909 A1 | 8/2013 | Dormanen et al. | |
| 2013/0314047 A1 | 11/2013 | Eagle et al. | |
| 2015/0364861 A1 * | 12/2015 | Lucke | A61M 1/1008 439/271 |

\* cited by examiner

COMPLIANT IMPLANTABLE CONNECTOR AND METHODS OF USE AND MANUFACTURE

CROSS-REFERENCES TO RELATED APPLICATIONS

This application claims the benefit of U.S. Provisional Application No. 62/332,987, filed on May 6, 2016, and entitled "COMPLIANT IMPLANTABLE CONNECTOR AND METHODS OF USE AND MANUFACTURE," the entirety of which is hereby incorporated herein by reference.

BACKGROUND

Implantable medical devices that are electrically powered have become ubiquitous in recent years. There are a wide range of such devices from neurostimulation devices, pacemakers, and cochlear implants to ventricular assist devices, known as VADs. Typically, such devices require transmission of data, power, and/or electrical control signals across leads or cables from a power source and controller to the implanted device. Different types of device can have vastly different power requirements and use cases such that cables and associated connectors that are suitable for one type of device may not suitable for another type of device. For example, neurostimulation devices are relatively low power devices that often utilize an implanted lead that is electrically connected to a header of an implanted pulse generator through a series of canted coil springs, such as a Bal Spring type connector. While these types of connectors have proven effective and dependable for many electrostimulation applications, these types of connectors may be generally unsuitable for other implanted medical devices such as those with relatively high power requirements (due to the high resistance associated with the canted coil spring design).

One type of implanted medical device having heightened power requirements is a VAD, which requires relatively high current and continuous voltage requirements as compared to pacemakers, which typically have low and intermittent power requirements. Since loss of power to an implanted VAD or failure to recharge an associated power supply poses life threatening consequences, to ensure continuous operation of the VAD, any connector used with an associated power cable or driveline cable must provide a dependable electrical connection for an extended period of time. Implanting electrical connectors suitable for higher power requirements within the body can be challenging due to the cyclical stresses and strains attributed to flexure and movement of cords and devices within the body. For this reason, many such VAD systems are powered through a driveline that is hardwired directly to the implanted pump with any connectors located outside the body or at least away from the heart in locations that are more stable and readily accessible.

Another challenge with an implanted connector is that the fluid-filled environment within the human body can be corrosive to connector materials conventionally used in high-powered connectors, such as stainless steel and copper. While certain non-corrosive alloys, such as a platinum iridium alloy (Pt—Ir), can be used, this material is exceedingly expensive and has mechanical properties that make its use in an implantable connector challenging (e.g., brittleness).

Accordingly, various alternative connectors have been proposed or theorized. Given the design challenges associated with implantable device, however, many of these are overly bulky and expensive. Therefore, there is a need for an improved connector to address these and other problems. There is a need for an implantable connector suitable for use with higher power requirements that is durable and corrosion resistant, while providing improved electrical and mechanical properties at a reduced cost of materials and manufacture. It is further desirable for such connectors to be viable in a design having reduced dimensions so as to be suitable for implantation at various locations within the body.

BRIEF SUMMARY

This application relates generally to connectors, and in particular to implantable connectors that carry power and control signals to an implanted medical device.

In one aspect, the invention pertains to implantable connectors adapted for use with a driveline cable that powers a mechanical circulatory support device, such as a VAD. Such connectors can be used to connect the driveline to an implanted rechargeable battery power source, connect the driveline to the pump or as an in-line connector. The implantable connectors described herein are suitable for drivelines implanted entirely within the body, percutaneous driveline cables that extend outside the body through an incision in the skin, or an external modular driveline. In certain embodiments, the connectors can be used with power cables suitable for powering any electrical device, implantable or otherwise, in either a direct current (DC) or alternating current (AC) application.

In various embodiments, the invention pertains to an implantable connector that includes a male component having one or more male contact pins and a female component having one or more female contact pins. Each contact pin includes a distal engaging surface on a distal portion thereof that is adapted for engaging with the distal engaging surface of a corresponding contact pin. The male and female components are adapted to interface to conductively couple the distal engaging surfaces of corresponding male and female pins arranged within. One or both of corresponding male and female contact pins includes an urging member proximal of the respective distal portion. The urging member is adapted to exert a reaction force in a longitudinal direction when axially displaced along a longitudinal axis of the respective contact pin to increase a contact force between distal engaging surface of corresponding male and female pins when conductively coupled in the connector. In some embodiments, the urging member is integral with the contact pin. For example, the urging member can be a portion of the contact pin that has been machined to function as an urging member or spring-like member. In some embodiments, the urging member is a helical cut portion defined in a hollowed portion of the respective contact pin. In some embodiments, only one of the corresponding male and female contact pins includes an urging member, while in other embodiments, both male and female contact pins include an urging member.

In various embodiments, the implantable connector includes corresponding male and female contact pins that are formed of a corrosion resistant metal alloy, such as platinum-iridium. In some embodiments, the helical cut portion is formed in a contact pin formed of platinum-iridium and defined to form the urging member having a sufficient spring constant to provide at least a desired contact force. The desired contact force can be a minimum contact force, or any force within a suitable range of contact forces. While typically, the helical cut is formed in a hollowed portion, it is appreciated that various other design can be used to form a spring-like urging member, for example, a braided design or a resilient hinge-type design.

In some embodiments, the distal engaging surfaces of corresponding male and female pins are defined as a protrusion and recessed portion, respectively. For example, the distal engaging surface of the male contact pin can be defined as a convex surface while the distal engaging surface of the female contact pin can be defined as a concave surface. In some embodiments, the concave and convex surfaces are each defined as semi-spheroidal surfaces, such as in a ball and cup design. In some embodiments, the male and female contacts pins are formed from a solid metal pin. In some embodiments, the male and female contacts can include, or be machined to include, a hollow portion in which a helical cut portion is defined. The helical cut portion can be defined to form a single helical member, or multiple helical members, such as a double-helix or a quadruple helix.

In another aspect, the invention allows for an implantable connector that utilizes electrical contacts formed of corrosion resistant alloy and maintains sufficient contact force between electrical contacts to be suitable for use in transmission of voltage and current for high powered implanted medical devices. In some embodiments, the electrical contacts are contact pins having a geometry that allows for flexibility and compliance in a longitudinal direction of the contact pin so as to provide the desired contact force when axially compressed when conductively coupled within the connector. The geometry can be defined to provide a desired contact force, while the size and shape of the interfacing surfaces of the contacts distribute the contact force to reduce stresses and strain within the contacts to avoid plastic deformation or failure of the contact material. In some embodiments, the interfacing contact surfaces are defined to distribute force to keep stress and strain below a yield strength of the contact material. In some embodiments, the desired contact force is a total axial contact force. Thus, in some embodiments, the size and shape of the interfacing contact surfaces can be defined as a function of the material properties of the contacts and the contact force provided by the connector geometry. This may allow for increased longevity of several years or more, even when subjected to cyclical stresses associated with implanted devices. In various embodiments, the geometry includes a helical cut portion defined within a proximal portion of the contact. In some embodiments, the electrical contact pins are dimensioned to be less than 10 mm in length, one or both of corresponding male and female contact pins including a proximal urging member as described above. Male and female contact pins can be defined according to various different dimensions, sizes and configurations. In various embodiments, male and female contact pins including the wire attachment portion, which is crimped, welded, or soldered to the conductor, can be about 5 mm to 50 mm in length, more typically about 10 mm to 20 mm in length. Male and female contact pins can be straight or angled (e.g., 90 degrees from the contact end to wire the conductor attachment end). In various embodiments, the nested male and female pin set can be in the range of about 5 mm to 60 mm in length, more typically about 15 mm to 40 mm in length. In various embodiments, overall connector length can be in the range of about 15 mm to 75 mm, more typically about 25 mm to 65 mm. In some embodiments, the contact pins are arranged in male and female components that are adapted to interface in a mated configuration, in which the respective urging member of the corresponding male and female contact pins is axially displaced a distance sufficient to exert the desired contact force.

In one aspect, the invention allows for an implantable connector having electrical contacts formed of materials with general material properties that are unsuitable for conventional connector geometries. As shown in the various embodiments described herein, the geometry of the urging member in conjunction with the interfacing contact surfaces allows the electrical contacts to be sufficiently engaged at a desired contact force (e.g., total axial contact force, localized contact force, radial compressive force) while stresses and strains within the contacts are maintained within a suitable range to avoid plastic deformation or fracture of the contact material, thereby maintaining integrity and longevity of the electrical connector. In some embodiments, the geometry of the connector is designed to keep localized forces within the contacts within an acceptable range for contact materials having low yield strength. In other embodiments, the geometry of the connector is designed to keep localized forces within the contacts within an acceptable range for contact materials that are brittle. It is appreciated that the size and shape of the interfacing contact surfaces affect the distribution of the reaction force, and in turn, the distribution of stress and strain within the material.

In some embodiments, the connector is suitable for providing a peak power of about 5 W or greater over an extended period of time. The connector can be suitable for use with AC or DC power. In some embodiments, the connector is adapted for coupling an implanted medical device to a power source and/or controller. The medical device can be an implantable VAD, such as any of those described herein.

In another aspect, methods of powering an implanted medical device using an improved implantable connector are described herein. Such a method can include interfacing a male component and female component, the male component including a plurality of male contact pins that correspond with a plurality of female contact pins of the female component, one or both of each corresponding male and female pin of the plurality including an urging member that exerts a reaction force when displaced. One of the male and female component can be associated with an implanted medical device while the other of the male and female component is associated with a power source or associated cable. Interfacing a male component of an implantable connector with a female component of the implantable connector so as to interface each corresponding male and female contact pin. The male and female components are matingly engaged in a mated position so that corresponding male and female contact pins are conductively coupled while the urging member is displaced along a longitudinal axis of the respective male and/or female pin. Electrical integrity of the conductive coupling is maintained by accommodating compliant movement between male and female components while a reaction force of the displaced urging member increases the contact force between conductively coupled corresponding male and female contact pins. In some embodiments, the urging member is a helical cut portion of the respective contact pin such that the reaction force is a spring force. The method can further include displacing the helical cut portion of the respective contact pin a distance sufficient to exert a desired contact force between conductively coupled corresponding male and female contact pins. Displacing the helical cut portion can be performed by matingly engaging the male and female components in a mated configuration. In some embodiments, interfacing surfaces of the contacts are defined with a geometry to facilitate distribution of the contact force within the contact material, such that the method includes distributing the contact force along the interfacing contact surfaces to maintain stress and strain within the contacts to avoid plastic deformation or failure of the contact material. In some embodiments, the interfacing surfaces are defined to distribute contact forces suitably for materials having low yield strength. In other embodiments, the interfacing surfaces are defined to distribute contact forces suitably for materials that are brittle.

In another aspect, methods of manufacturing an implantable connector having improved properties are provided herein. Such methods can include defining a distally protruding surface in a distal portion of each of one or more male contact pins and defining a recessed surface in a distal portion of each of one or more female contact pins so as to correspond to the shape of the protruding surface in the respective male contact pin. A helical cut portion can be defined in a portion of the male and/or female pin proximal of the distal portion thereof. An electrical conductor can be electrically coupled to each of the one or more female pins as well as each of the one or more male pins, such as by laser welding or crimping. The male and female contact pins are incorporated into interfacing male and female components, respectively. The method can further include adapting the male and female components to interface with each other so that the one or more male and female components are conductively coupled while the helical portion of each respective male and/or female contact pin is displaced to exert a spring force in response that increases a contact force between conductively coupled contact pins. In some embodiments, a geometry of an interfacing portion of each of the male and female components can be formed to define a mated configuration in which the helical portion is displaced a sufficient distance to provide a desired contact force between conductively coupled contact pins.

DETAILED DESCRIPTION

The invention relates generally to electrical connectors, and in particular to implantable connectors for use with power cables for powering high-powered implanted medical devices, such as a mechanical circulatory support system or VADs.

Developing connectors that are implanted in the human body is challenging, particularly for connectors that are designed to be connected and disconnected in a biological environment. The electrical contact set lies at the heart of any connector design. Current research and testing has demonstrated that electrical contacts that are subjected to a biologic environment are susceptible to corrosion—the biggest risk for implantable connector designs. The most robust material to address the corrosion issue in electrical contacts is a blend of a platinum-iridium alloy. Unfortunately, there are considerable challenges associated with use of platinum-iridium alloy for electrical contact designs. This material inherently has certain drawbacks, including exceedingly high cost and limited basic mechanical properties of the material (e.g., Yield Strength, Young's Modulus, brittleness). These materials may also have insufficient plastic deformation properties for certain applications. Current commercially available connectors fail to provide a corrosion resistant design that satisfactorily addresses these issues. The invention allows for an implantable connector having an electrical contact set that largely resolves the above noted issues, while providing a robust and durable electrical connection for use with high-powered implanted medical devices.

In various embodiments, the invention provides an implantable connector having a male and female component that matingly engage so as to conductively couple corresponding contact pins arranged within. One or both of the contact pins includes an urging member that provides a desired contact force between contact pins to maintain electrical integrity of the connection over an extended period of time. In one aspect, the urging member is adapted to provide the desired contact force while stresses remain low enough to avoid risk of creep or plastic deformation of the contact pins. In some embodiments, the urging member is provided in only the male contact pin or the female contact pin, while in other embodiments, an urging member is included in both the male and female contact pins. The urging member can be a spring or other such resilient member that exerts sufficient force when axially displaced by mating engagement of the male and female components to provide a desired contact force between corresponding male and female contact pins. The desired contact forces depend largely on the voltages and currents being transmitted, as well as the particular geometry of the components. For example, in some embodiments, contact forces can range from about 100 grams to 1,000 grams.

In general, improved contact forces and/or surface area leads to an improvement in electrical performance. In certain applications, maintaining continuous minimum contact for transmission is even more important than average or peak power transmission. As the contact force increases, the highly localized stress created by contact (e.g., Hertz stresses) experienced by the areas in contact will increase. This means that the highest peaks in contact will yield, expanding the contact area in an effort to counter the additional force. The mating surfaces will then move closer together which allows contact to be made at shorter, wider peaks on both surfaces. This decreases the constriction resistance since there are now more and larger paths for the signal to travel through. Since the contacting surfaces are wider, electrical signals can more easily pass through any film that might exist. Therefore, any film resistance decreases as well. Thus, increased contact force allows the signal to travel across the interface much more easily. At very high contact forces, most of the total resistance of the connector comes from bulk resistance. The resistance is also more stable, since a small change in force will result in a minimal change in contact resistance. Conversely, as contact force decreases, fewer areas will remain in contact, thereby degrading electrical performance and stability of resistance. The advantages of providing improved contact forces can be further understood by referring to *The Importance of Contact Force*, Technical Tidbits, Issue No. 6—July 2009, the entire contents of which are incorporated herein by reference.

In some embodiments, each of the corresponding male and female contact pins extend along a longitudinal axis and are conductively coupled by engaging corresponding distal surfaces on a distal portion of each of the corresponding pins. The urging member is disposed at a location proximal of the distal portion of one or both pins and exerts an urging force in a direction along the longitudinal axis to provide a contact force between engaging distal surfaces of corresponding pins.

In another aspect, a connector includes a male and female electrical contact set that has an integrated compliance feature built into either one or both of the contact pins. The primary advantages of this approach are that this design allows for more compact footprints and can be adapted to achieve proper contact forces between contact pins. It is appreciated that such designs can utilize multiple pin to pin interfaces, including but not limited to the ball and cup configuration described herein. This design is advantageous as it allows the male and female contact to accommodate compliant movement while remaining interface and conductively coupled. This design is also suitable for use with electrical contact pins formed of corrosion resistant materials like platinum-iridium alloys that are not traditional spring materials (i.e., beryllium copper, spring-tempered stainless steels). Secondary advantages of this approach include the ability of the electrical contacts to be able to take up compliance from relative movement between the two halves of the connector body that are subjected to cyclic motion (i.e., a beating heart which produces approximately 32 million cycles per year). Such an approach offers a number of advantages, which include a cost effective contact design by minimizing footprint and hence the cost of materials, improving ease of manufacturing through use of traditional machining operations and improving distribution and management of structural loads within the components. Importantly, this approach also allows for further considerably reduced connector sizes, which is vital for implanted devices, particularly next generation devices having substantially reduced size as compared to current devices. This approach also reduces the risk of interruptions in power transmission from poor contact between the male and female contacts.

In some embodiments, the urging member is formed in a portion of the respective contact pin by defining a helical cut in a portion of the contact pin such that the portion acts as spring being compressible along a longitudinal axis of the contact pin so as to exert a reaction force towards the interfacing distal surfaces of corresponding contact pins. Typically, the contact pin is hollow along the portion in which the helical cut is formed so as to facilitate a resilient spring action. The contacts pins and helical cut portions are dimensioned so that when the male and female components are matingly engaged the helical cut portion is displaced or compressed a small distance. The helical cut portion can be defined to have a spring constant that provides a desired contact force when compressed. The spring constant required to provide a desired contact force is a function of the material and dimensional properties of the contact pins as well as the distance by which the helical cut portion is compressed when the male and female components are mated. In some embodiments, the urging member (e.g., helical cut) could be put on only one of corresponding male and female contact pins, while in others the urging member could be integrated into both contact pins. Including such an urging member in both male and female contact pins allows for improved balance of stresses and loads and allows for more compliance and/or tune-ability of force, deflection, stress, and strain in the contact set. In addition, several other pin to pin interfaces could be explored as an alternative to a ball and cup design, for example, a flat pin to flat pin or a crowned pin to flat plate.

Figure 1A:
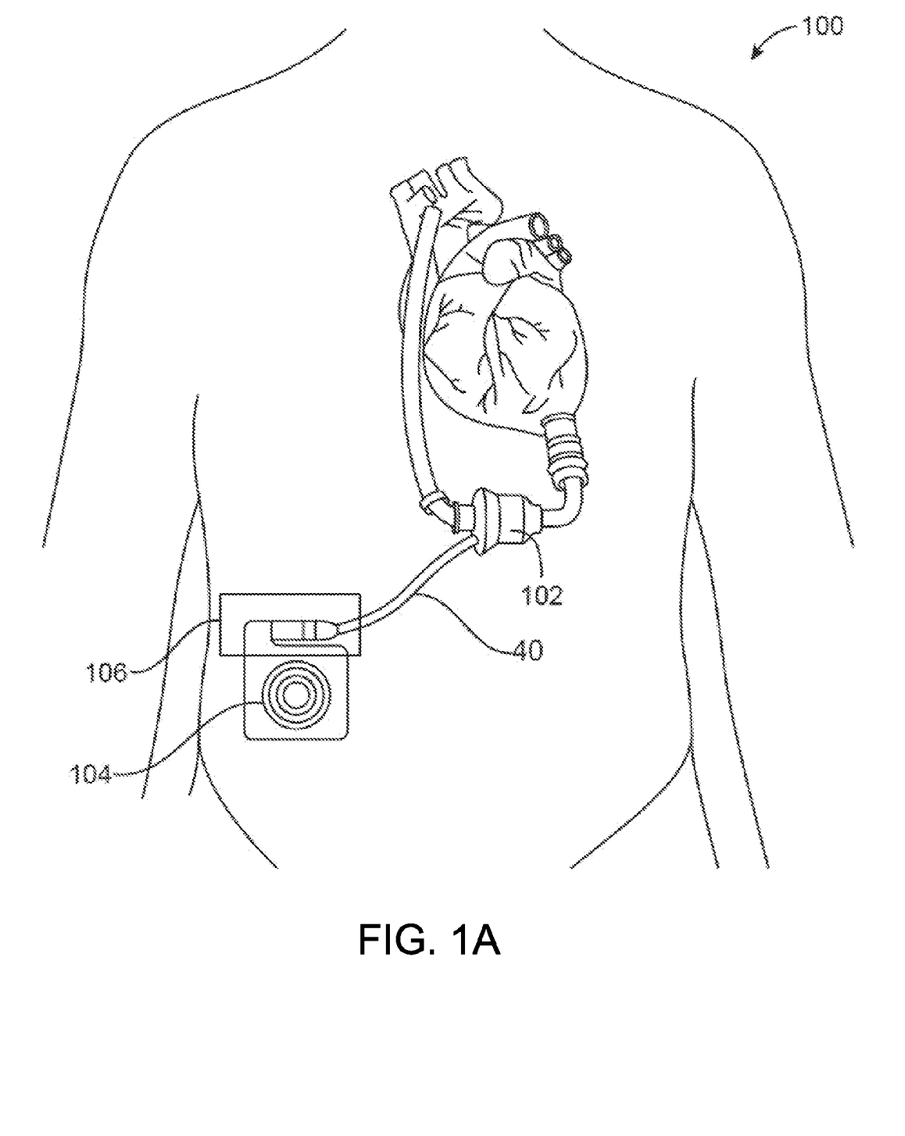
FIG. 1A is an illustration of a mechanical circulatory support system fully implanted in a patient's body with an associated driveline in accordance with embodiments of the invention.
Figure 1B:
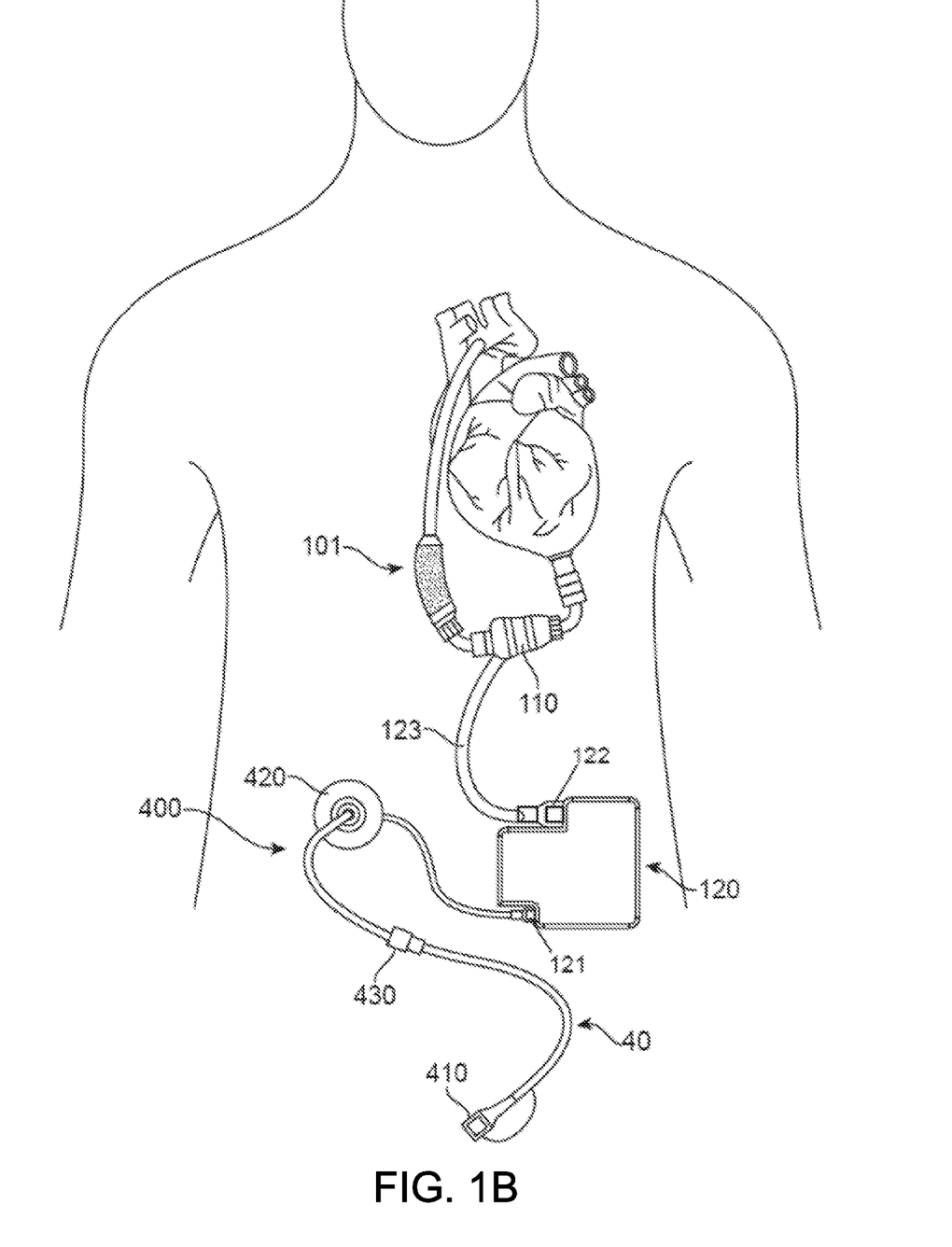
FIG. 1B is an illustration of a mechanical circulatory support system implanted in a patient's body with a modular driveline in accordance with aspects of the invention.

FIGS. 1A-1B illustrates implanted mechanical circulatory systems having driveline cables that are fully or partly implanted and that include implanted connectors. While the implanted connectors in these systems are shown in particular locations, it is appreciated that implantable connectors could be used in various other locations, for example between the driveline and the implanted blood pump or VAD, in accordance with aspects of the invention. Notably, the advantageous aspects of the implantable connectors described herein can allow for use of implanted connectors in locations and applications that previously would have been extremely challenging if not infeasible.

FIG. 1A illustrates an medical system 100 that includes an implantable medical device 102, shown as a VAD, and an implanted module 104 configured to receive wireless power from outside the body to provide power for the medical device. A bulkhead connector 106 and drive line cable 40 connect the implanted module to the medical device to provide power, data, and or/control signals from the module to the device. Such medical devices may be relatively high powered devices. In some embodiments, the module can supply ~5 W to drive the medical device. In some embodiments, power is supplied by applying voltages as low as 10 V or as high as 24 V if needed. In some applications, the implanted module is configured to remain inside the patient's body for a minimum of two years and to serve as the power source and controller for the medical device. The clinician can surgically replace the implanted module by disconnecting the existing driveline cable from the existing module, removing the existing module, and reconnecting the same driveline cable to a new module without removing the medical device. Similarly, a clinician can surgically replace the cable and/or medical device while leaving the implanted module in place. To provide a durable, reliable electrical connection between the power module and the driveline, the bulkhead connector 106 can be configured according to any of the aspects described herein.

Various aspects of such power cables are described in U.S. Pat. No. 8,562,508 entitled "Mobility-Enhancing Blood Pump System," filed Dec. 30, 2009; U.S. Application Publication No. 2012/0149229 entitled "Modular Driveline," published on Jun. 14, 2012; and U.S. Pat. No. 8,682,431 entitled "Driveline Cable Assembly," filed Jan. 23, 2013; each of which the entire contents are incorporated herein by reference for all purposes.

FIG. 1B illustrates another modular implanted ventricular assist device including an internal blood pump assembly 110, an internal controller assembly 120 connected to the blood pump assembly via an electrical conduit 123, internal rechargeable power storage device contained within the controller assembly 120, and a percutaneous lead 400 connected to the controller assembly 120 and exiting the body at an aperture port 420. The power storage device may include one or more "smart" lithium-chemistry batteries that are readily rechargeable. The distal end of driveline cable 40 includes a connector 410 for connection to an external power source for periodic charging of the internal power storage device of controller assembly 120. The percutaneous lead may connect to a driveline cable 40 at connector 430 such that the driveline cable can be removed and replaced as needed. In this embodiment, the blood pump 110 can be a VAD, which is a mechanical circulatory device that is used to partially or completely replace the function of a failing heart. Some VADs are intended for short term use, typically for patients recovering from heart attacks or heart surgery, while others are intended for long term use (e.g., years, and the remainder of a user's life), typically for patients suffering from congestive heart failure. VADs are designed to assist either the right (RVAD) or left (LVAD) ventricle, or both at once (BiVAD). VADs can be designed with an axial flow or centrifugal flow configuration. It should be appreciated that the technical features disclosed herein apply equally to any variation of the blood pump as described in this disclosure.

In this embodiment, the controller assembly 120 is connected to electrical conduit 123 at connector 122 and connected to percutaneous lead at 121. Each of connectors 121 and 122 can be removable to allow for ready detachment and replacement of the internal controller assembly 120 or the percutaneous lead 400 as needed. Since both connectors 121 and 122 are implanted and subject to corrosion as well as period flexure and movement, one or both of these connectors can be configured according to various aspects of the invention described herein. Such improved connectors allow for these improved mechanical and electrical properties and allow for a reduction in size, thereby allowing further miniaturization of the implanted systems described herein.

Related blood pumps applicable to the present invention are described in greater detail below and in U.S. Pat. Nos. 5,695,471; 6,071,093; 6,116,862; 6,186,665; 6,234,772; 6,264,635; 6,688,861; 7,699,586; 7,976,271; 7,997,854; 8,007,254; 8,152,493; 8,562,508; 8,652,024; and 8,668,473 and U.S. Patent Publication Nos. 2007/0078293; 2008/0021394; 2009/0203957; 2012/0046514; 2012/0095281; 2013/0096364; 2013/0170970; 2013/0121821; 2013/0127253; and 2013/0225909, all of which are incorporated herein by reference for all purposes in their entirety. Related controller systems applicable to the present invention are described in greater detail below and in U.S. Pat. Nos. 5,888,242; 6,991,595; 8,323,174; 8,449,444; 8,506,471; 8,597,350; and 8,657,733 and U.S. Patent Publication Nos. 2005/0071001 and 2013/0314047, all of which are incorporated herein by reference for all purposes in their entirety.

Figure 2A:
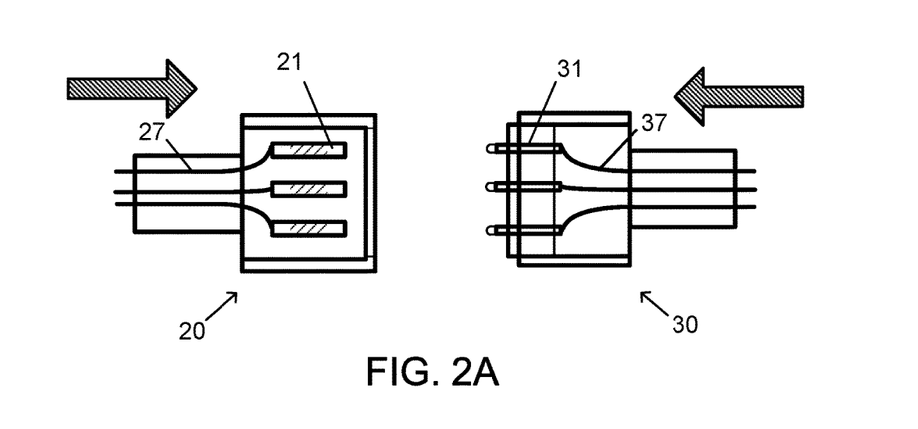
FIG. 2A is an illustration of an implantable connector before mating of male and female components in accordance with various embodiments.
Figure 2B:
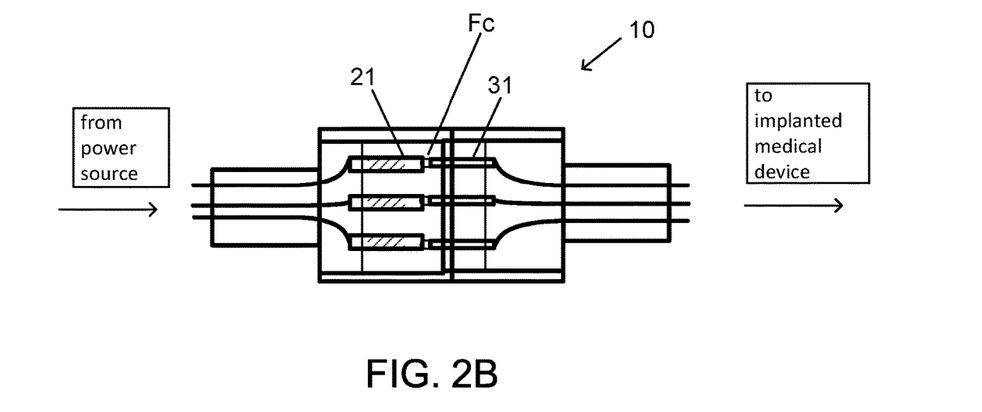
FIG. 2B is an illustration of an implantable connector with male and female components in a mated configuration in accordance with various embodiments.

FIGS. 2A-2B illustrate an exemplary embodiment of an implantable connector 10 having a female component 20 and a male component 30. Each of the male and female components includes corresponding electrical contacts that are conductively coupled when the male and female components are matingly engaged so as to allow transport of power and/or electrical control signals through the connector. Typically, such connectors are multi-pin connectors having multiple corresponding electrical contacts configured as needed for the requirements of a particular device or application. FIG. 2A illustrates the male and female components 30, 20 before assembly, while FIG. 2B illustrates connector 10 with male and female components 30, 20 in a mated configuration. The outer housing of each of the male and female component is shown as transparent to allow visibility of internal electrical contact sets therein. In this embodiment, the electrical contacts sets within connector 10 are electrical contact pins, the female component 20 having multiple female contact pins 21 arranged therein and the male component 30 having multiple male contact pins 31 disposed therein. The contact pins are typically elongate cylindrical pins. Each of male and female contact pins 31, 21 is electrically coupled at or near its proximal end to a respective conductor 37, 27. Typically, the contact pins are formed of a corrosion resistant metal alloy (e.g., a nickel-cobalt alloy such as MP35N) so as to provide resistance against the corrosive effects of the fluid-saturated environment within the body when implanted therein.

As can be seen in FIG. 2B, when male and female components 30, 20 are engaged in a mated configuration, the distal surfaces of each of the corresponding electrical contact pins 31, 21 are engaged so as to be conductively coupled. To ensure a reliable electrical connection suitable for transmission of higher voltages and currents associated with relatively high powered medical devices, such as VADs, the electrical contact pins should engage with a minimum contact force, Fc. It is appreciated the suitable contact force between contacts can vary widely based on the geometry of the electrical contacts, the transmitted power as well as the electrical requirements of the implanted medical devices. In various embodiments, contact forces can range from about 100 grams to 1000 grams. As described previously, insufficient contact force can cause increased resistance, which results in reduced efficiency and excess heat production, both of which are unacceptable in an implanted device.

To ensure a suitable contact force, Fc, one or both of corresponding contact pins includes an urging member proximal of the distal engaging surface to ensure sufficient contact force is applied and maintained. The urging member is designed specifically to apply the desired contact force, when male and female components 30, 20 are in the fully mated configuration. Typically, the mating configuration is determined by engaging corresponding surfaces of the male and female components, such as a distal outer surface of the male component 30 abutting against a recessed surface or inner lip circumscribing the distal opening of the female component 21. The mated configuration is typically secured by one or more retaining features (e.g., snap-fit, threaded screw, clearance fit, and the like). It is appreciated, however, that male and female components can be configured to interface in a mated configuration or retained in the mated configuration in any number of ways using various mechanisms, as would be known to one of skill in the art from the description herein.

Figure 3:
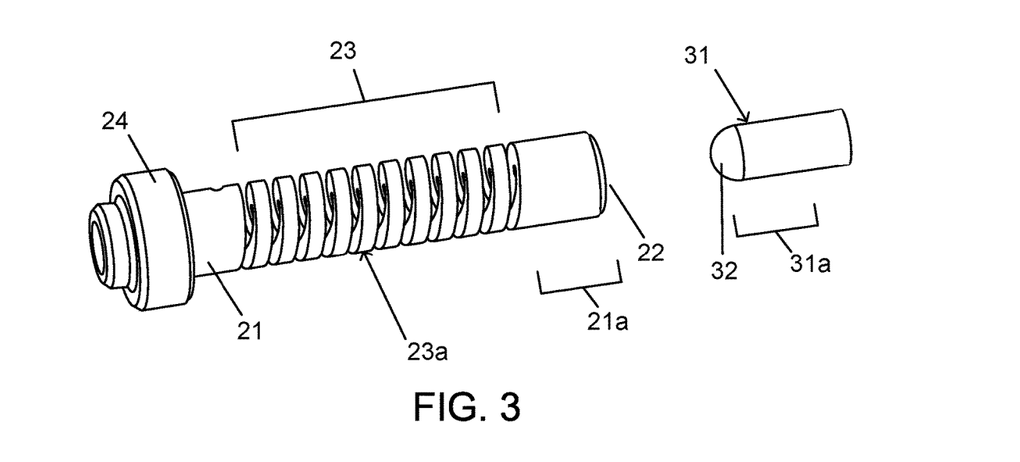
FIG. 3 is an illustration of male and female contact pins that include an integrated urging member for use in a connector in accordance with various embodiments.

FIG. 3 illustrates a detail view of an example female contact pin 21 and corresponding male contact pin 31 for use within a connector 10 in accordance with aspects of the invention. Each of female contact pin 21 and male contact pin 31 is a cylindrical metal pin formed of a corrosion resistant material, such as Pt—Ir. Female contact pin 21 extends from a proximal base 24 to a distal engaging surface 22 defined in a distal portion or region 21a of the pin. Distal engaging surface 22 is adapted for conductively engaging with a corresponding distal engaging surface 32 defined in a distal portion or region 31a of male contact pin 31. Proximal base 24 can be coupled within female component 30 so as to arrange female contact pin 21 in a position corresponding to the male contact pins 31 arranged within the male component 30. Male contact pins 31 can also include a base portion (not shown) by which the contact pins are coupled within the male component 20.

In this embodiment, the distal engaging surfaces 32, 22 of male and female contact pins 31, 21 are configured according to a ball and cup type design. In this design, the distal engaging surface 22 of female contact pin 21 is a recessed portion defined as a semi-spherical concave surface, while the corresponding distal engaging surface 32 of the male contact pin 31 is a protruding portion defined as a semi-spherical convex surface. Corresponding distal engaging surfaces 22, 32 are dimensioned so as to fittingly engage, as shown in the cross-section of FIG. 4, to provide a conductive couple male and female contact pins. These corresponding engaging surface also help maintain conductive coupling between male and female contact pins 21, 31 when the device or cable coupled by the connector are subjected to movement or flexure as this design allows for some off-axis relative movement between male and female contact pins. While a ball and cup type configuration is depicted here, it is appreciated that corresponding distal engaging surface could be defined according to various other designs, for example, a protruding cone received in a conical recess, a flat pin of any shape received in a corresponding hole, or any protruding feature adapted to be fittingly received within a corresponding recessed feature. Typically, such interfaces are configured to allow the male and female connectors to accommodate compliant movement, such as may occur due to cyclical stresses and strains or movement of associated components, while maintaining conductive coupling between male and female contacts.

In this embodiment, female contact pin 21 includes urging member 23 defined as a helical cut potion 23a in a proximal portion thereof. The helical cut can be created by use of standard machining techniques and is defined in a hollowed portion of the contact pin such that the remaining helical element acts as a spring that can be compressed when male and female pins 21, 31 are engaged so as to exert a biasing or urging force longitudinally directed along the pin, which increases contact forces between corresponding distal engaging surfaces. Helical cut portion 23a can be designed to form a spring of a particular spring constant so as to exert a desired contact force pre-determined for a particular application or device. Typically, the particular helical cut design created is a function of the geometry of the contact pin (e.g., a side-wall thickness of the contact pin along the hollow portion, diameter of the contact pin), the material properties of the contact pin, a range of suitable displacements of the spring when the connector is mated, and the contact forces desired. It is appreciated that various helical cut designs can be used to provide a desired contact force. For example, variations in pitch of the helical cut portion can allow for longer or shorter sections that have the same spring constant capable of providing the desired contact forces. In some embodiments, the urging member can include any pattern or design adapted to provide an urging force in a longitudinal direction, for example, by use of a zig-zag, sinusoidal, or coil shaped members or a woven structure or stent-type design.

As can be seen in FIG. 3, the distal engaging surfaces 22, 32 are engaged by advancing male and female contact pins 31, 21 toward each other along their respective longitudinal axes. Continued advancement of the contact pins axially displaces the helical cut portion 23a along its longitudinal axis such that a reaction force of the urging member exerts the contact force, Fc, between the distal engaging surfaces 22, 32. The applied force required to compress the urging member a particular distance can be determined by the spring constant, k, of the helical cut urging member according to the spring constant formula, $F=-kx$. In such a configuration, the reaction force providing the contact force would be equal to the applied force. Thus, it can be seen that the helical cut portion can be defined to create the desired contact force between the engaged distal engaging surfaces of the contact pins. In turn, the contact force can also be adjusted by configuring the male and female components to mate so as to cause a particular displacement of the urging member, thereby creating a reaction force that provides the desired contact force.

In some embodiments, each corresponding connector pin is of a relatively small length, such as between 5-25 mm. The helical cut portion can be included along a portion proximal of the distal portion, the portion being extending along a substantial length of the contact pin, for example between about 10% to about 90% of the length of the contact pin. In various embodiments, the helical cut portion extends along at least about 25% of the length of the contact pin, at least about 50% of the length of the contact pin, or at least about 75% of the length of the contact pin. In various embodiments, the helical cut portion extends only along a distalmost end of the contact pin. Typically, in embodiments where corresponding contact pins are about 10 mm or less, the helical cut portion is compressed only about 2-5 mm, which can be a portion of a fully displaced or compressed state or the entire displacement distance. This aspect allows for a connector of a reduced footprint, which allows for implantation of the connector in various locations that were not previously feasible due to the bulk and expense of previously proposed designs. It is appreciated that the concepts described herein are not limited to connectors of any particular size and can be applied to contact pins of various other dimensions, substantially smaller or larger than those described.

Figure 4:
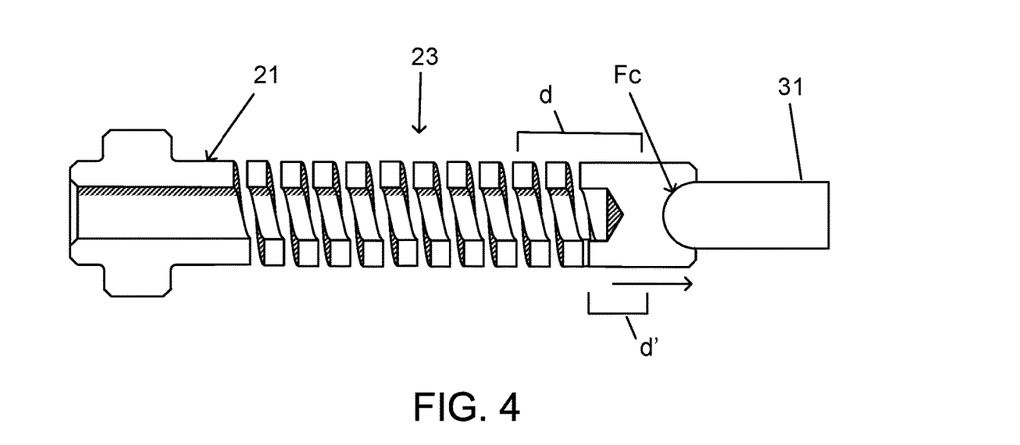
FIG. 4 is a cross-section of an implantable connector in a mated configuration in accordance with various embodiments

FIG. 4 depicts the male and female contact pins 21, 31 conductively coupled, as they would be in the mated configuration of the connector. As defined here, the helical cut urging member 23 can be axially compressed a total displacement, d. In this embodiment, when in the mated configuration, the helical cut urging member 23 is axially displaced by a partial displacement, d', while the distal engaging surfaces are engaged and therefore conductively coupled. The axial displacement of the urging member 23 provides a reaction force that exerts contact force, Fc, between the engaged distal engaging surfaces 22, 32. While in this embodiment the urging member is displaced only a partial displacement, d', it is appreciated that, in some embodiments, the urging member can be fully displaced when in the mated configuration. There may be certain advantages associated with each configuration. For example, by providing such a connector with one or more urging members that are only partially axially displaced in the mated configuration, the connector can provide some additional flexibility of the urging member in either axial direction, while maintaining contact between distal engaging surfaces of the corresponding contact pins. Alternatively, by providing such a connector with one or more urging members that are fully axially displaced in the mated configuration, the potential for creep within the material of the urging member can be eliminated.

In various embodiments, the male and female components, as well as the contact pins, can be configured to control the amount of displacement of the urging member in the mated configuration such that the contact force can be "tuned" as desired. For example, the male and female components can include an adjustable feature that allows the distance by which urging member is displaced to be adjusted, thereby increase or decreasing the resulting reaction force and contact force as desired. In another example, the contact pins could be placed at a greater depth within respective male or female components so as to control the displacement of the urging member and thereby provide the desired contact force.

Figure 5A:
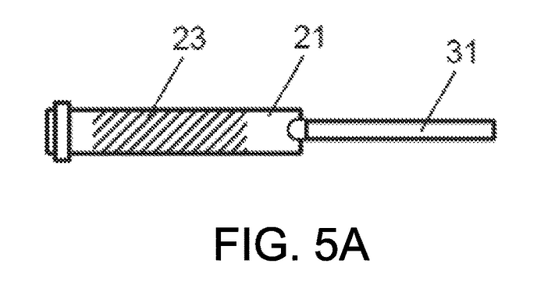
FIGS. 5A-5C are examples of alternative configurations of male and female contact pins for use in a connector in accordance with various embodiments.
Figure 5B:
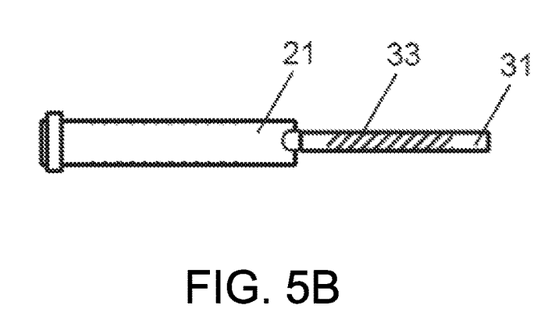
Figure 5C:
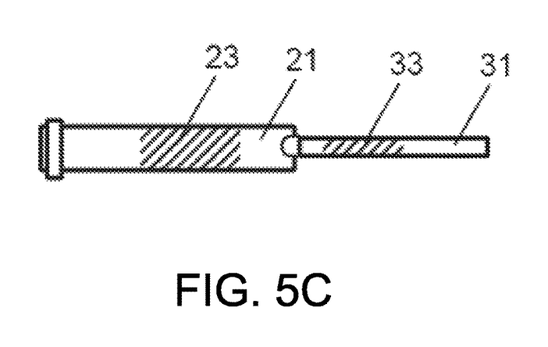

FIGS. 5A-5C illustrates various example pin configurations for use in an improved implantable connector in accordance with various embodiments. FIG. 5A depicts male and female contact pins 31, 21 with a helical cut urging member 23 provided in a proximal portion of the female contact pin 21. FIG. 5B depicts male and female contact pins 31, 21 with a helical cut urging member 33 provided in the male contact pin 31. FIG. 5C depicts male and female contact pins 31, 21, each with a helical cut urging member 23, 33 provided in a proximal portion thereof.

The type of configuration used in the connector can be selected according to a particular need or application, for example, selection can based on the amount and direction of any expected relative movement between devices and/or cables being connected. The configuration in FIG. 5C is advantageous because the stresses and strains exerted through the connector are shared or balanced between pins. This can improve the longevity and mechanical properties of the connector. Since this further reduces the stresses and strains endured by the urging member, the size and thickness of the electrical contact pins can be scaled down further, thereby further reducing the size and cost of the connector. In addition, as can be seen in FIGS. 5A-5C, by including an urging member in both male and female contact pins, such as in FIG. 5C, the length and/or size of the urging member can be reduced as compared to embodiments where the urging member is provided in only one contact pin, such as in FIGS. 5A-5B.

Figure 6:
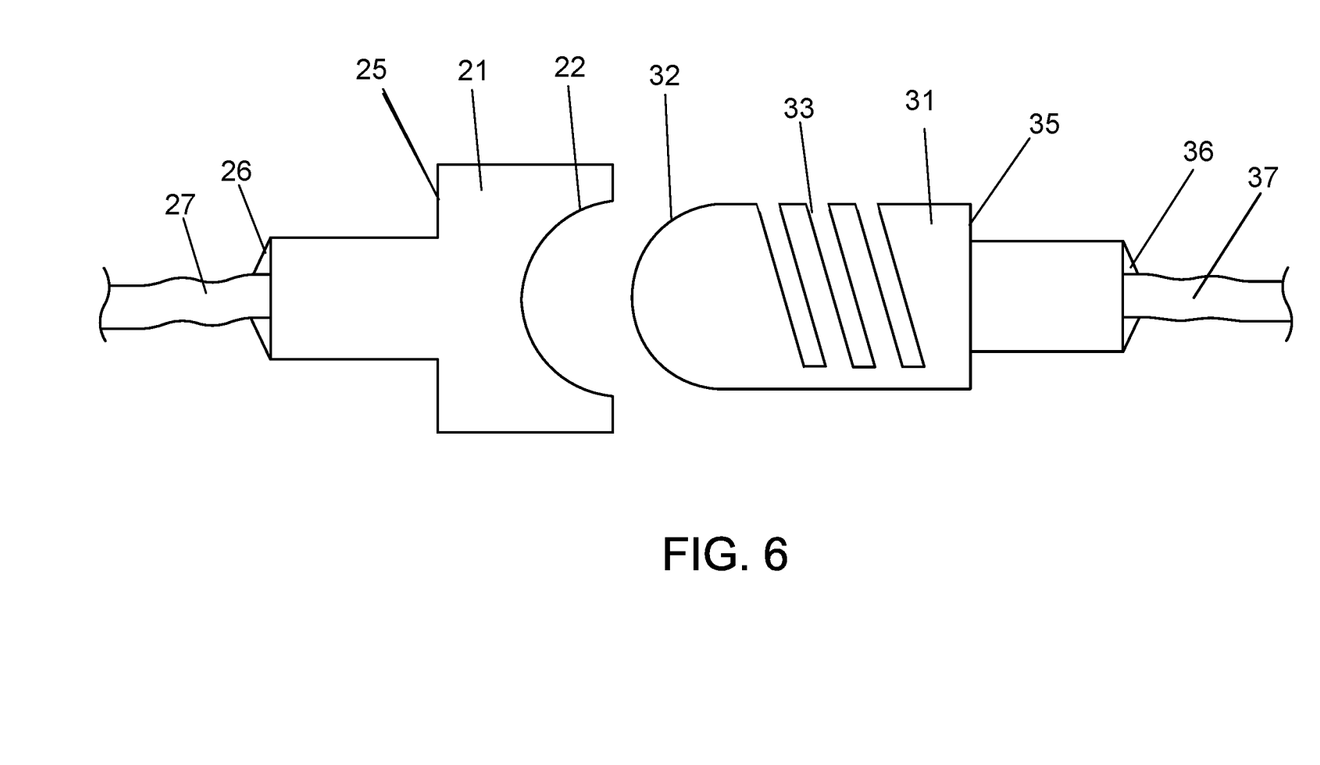
FIG. 6 is another illustration of an implantable connector in accordance with various embodiments.

FIG. 6 depicts an alternative embodiment of a female contact pin 21 and a male contact pin 31 that includes an integral urging member defined by a helical cut portion 33. As in previously described embodiments, the male and female contact pins 31, 21 include corresponding distal engaging surfaces 32, 22, respectively, defined according to a ball and cup design. In this embodiment, each of the female and male contact pins 31, 21 includes a hard stop shoulder 35, 25 that faces in a proximal direction for each respective contact pin. In each contact pin, the hard stop shoulder interfaces with a corresponding surface within corresponding male and female components of the connector. When in the mated configuration, corresponding surfaces in the male and female components abut against the hard stop shoulder and force corresponding contacts pins together to conductively couple corresponding distal engaging surfaces and displace the helical cut urging member sufficiently to provide a desired contact force. Such a configuration is appropriate particularly since contact bodies that house contact pins are typically a non-conductive material, such as plastic. A hard stop shoulder provides good mechanical stability and reduces reaction forces at the interface. Each of male and female contact pins 31, 21 is electrically coupled at or near its proximal end to a respective conductor 37, 27 at corresponding shoulder joints 36, 26, respectively. It is appreciated that these embodiments described are merely illustrative and that similar type male and female contact pins having one or more urging members providing a longitudinal reaction force in response to axial displacement could be incorporated and arranged within a connector in any number of ways as would be known to one of skill in the art from the description herein.

Figure 7:
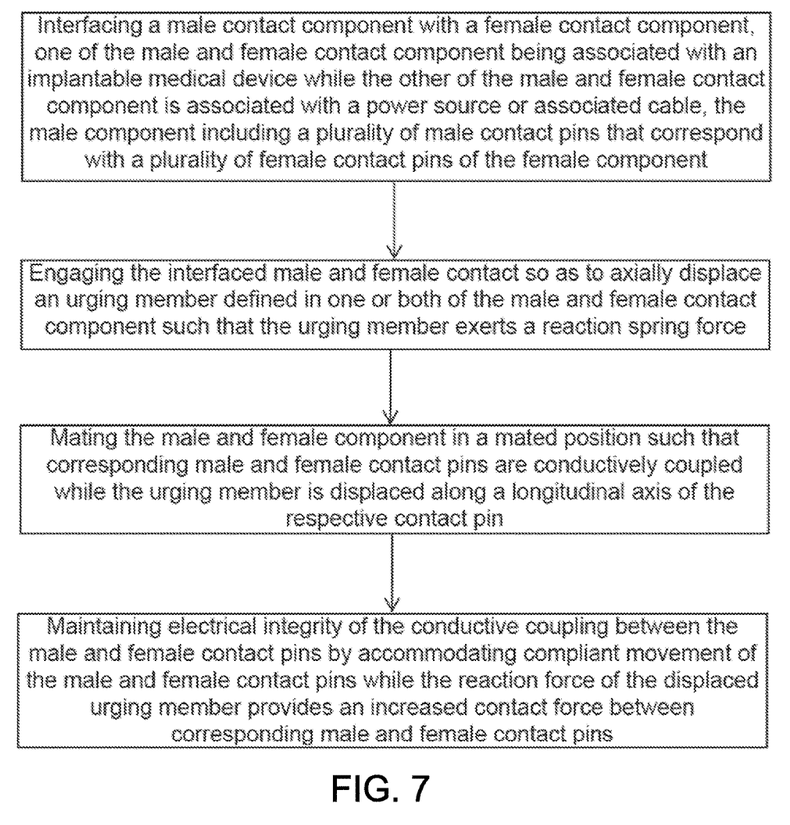
FIG. 7 illustrates a method of powering an implanted medical device with an implantable connector in accordance with various embodiments.

FIG. 7 illustrates a method of powering an implanted medical device with an implantable connector in accordance with various embodiments. Such methods can include interfacing a male contact component with a female contact component, one of the male and female contact component being associated with an implantable medical device while the other of the male and female contact component is associated with a power source or associated cable, the male component including multiple male contact pins that correspond with multiple female contact pins of the female component. The interfaced male and female contact are then engaged so as to axially displace an urging member defined in one or both of the male and female contact component such that the urging member exerts a reaction spring force. The male and female component are then mated in a mated position in which corresponding male and female contact pins are conductively coupled while the urging member is displaced along a longitudinal axis of the respective contact pin. Electrical integrity of the conductive coupling between the male and female contact pins is maintained by accommodating compliant movement of the male and female contact pins while the reaction force of the displaced urging member provides an increased contact force between corresponding male and female contact pins.

Figure 8:
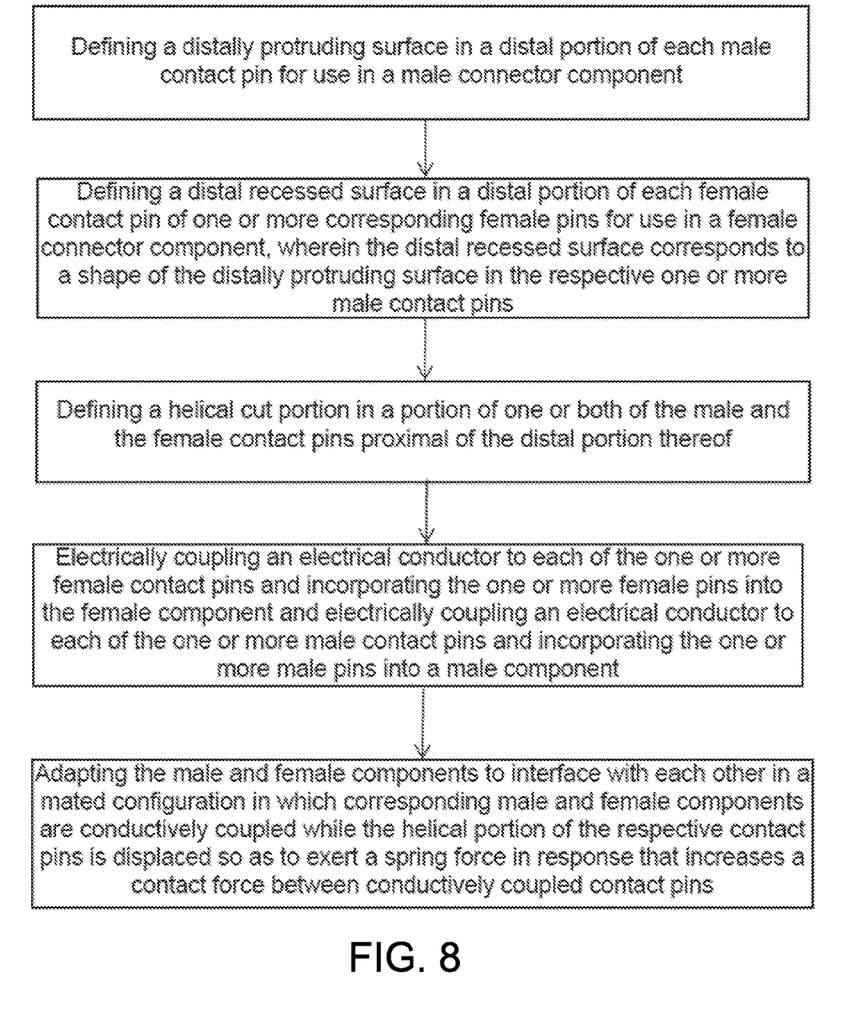
FIG. 8 illustrates a method of manufacturing an implantable connector in accordance with various embodiments.

FIG. 8 illustrates a method of manufacturing an implantable connector in accordance with various embodiments. Such methods can include defining a distally protruding surface in a distal portion of each male contact pin for use in a male connector component and defining a distal recessed surface in a distal portion of each female contact pin of one or more corresponding female pins for use in a female connector component, wherein the distal recessed surface corresponds to a shape of the distally protruding surface in the respective one or more male contact pins. An urging member is then incorporated into one or both of the male and female components. In some embodiments, incorporating the urging member includes defining a helical cut portion in a portion of one or both of the male and the female contact pins proximal of the distal portion thereof. The method can further include electrically coupling an electrical conductor to each of the one or more female contact pins and incorporating the one or more female pins into the female component and electrically coupling an electrical conductor to each of the one or more male contact pins and incorporating the one or more male pins into a male component. To maintain electrical integrity of the connection over time, the method can further include adapting the male and female components to interface with each other in a mated configuration in which corresponding male and female components are conductively coupled while the helical portion of the respective contact pins is displaced so as to exert a spring force in response that increases a contact force between conductively coupled contact pins.

Although the invention is described in terms of an implantable connector for a driveline for a VAD, one will appreciate that the invention may be applied equally to connectors adapted for use with various other devices and applications. It is further appreciated that the invention can be applicable to any connector, including non-implantable connectors used in medical and non-medical applications.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. An implantable connector having interfacing male and female components and adapted for use with an implanted medical device, the connector comprising:
   one or more male contact pins of the male component, each male contact pin having a proximal portion coupled to a conductor and a distal portion having a distal engaging surface defined therein; and
   one or more female contact pins of the female component, each female contact pin having a proximal portion coupled to a conductor and a distal portion having a distal engaging surface defined therein that is adapted for engaging with the distal engaging surface of the corresponding male contact pin;
   wherein one or both of the corresponding male and female contact pins include an urging member defined in a portion of the respective pin proximal of the distal portion thereof, wherein the urging member comprises a helical cut portion defined along a hollow portion of the respective contact pin, the urging member configured to exert a reaction force in a longitudinal direction when displaced along a longitudinal axis of the respective contact pin to increase a contact force between engaging surfaces of the corresponding male and female pins when conductively coupled.

2. The implantable connector of claim 1, wherein each of the female contact pins includes the helical cut portion.

3. The implantable connector of claim 1, wherein each of the male contact pins includes the helical cut portion.

4. The implantable connector of claim 1, wherein each of corresponding male and female contact pins includes the helical cut portion.

5. The implantable connector of claim 1, wherein each of the male and female contact pins are formed of a corrosive resistant metal alloy.

6. The implantable connector of claim 5, wherein each of the male and female contact pins are formed of a platinum iridium alloy.

7. The implantable connector of claim 1, wherein the distal engaging surface of each of the one or more male contact pins is a protruding surface.

8. The implantable connector of claim 7, wherein the distal engaging surface of each of the one more female contact pins is a recessed surface.

9. The implantable connector of claim 8, wherein the protruding surface is a convex surface.

10. The implantable connector of claim 9, wherein the recessed surface is a concave surface.

11. The implantable connector of claim 10, wherein each of the convex and concave surfaces is a semi-spherical surface.

12. The implantable connector of claim 1, wherein one or both of the male and female contact pins is formed of a solid metal pin.

13. The implantable connector of claim 1, wherein helical portion comprises any of: a single helical element, a double-helical element, and four parallel helical elements.

14. The implantable connector of claim 1, wherein the male and female components are adapted to interface in a mated configuration that axially displaces the helical cut portion a distance sufficient to exert a desired contact force.

15. The implantable connector of claim 1, wherein each of the male and contact pins is less than 10 mm in length.

16. The implantable connector of claim 1, wherein the cable is suitable for providing a peak power of about 5 W or greater over an extended period of time.

17. The implantable connector of claim 16, wherein the implanted medical device is an implantable heart pump and the connector is adapted for coupling the implantable heart pump to a power source and/or controller.

18. A method of powering an implantable medical device, the method comprising:
   interfacing a male contact component with a female contact component, one of the male and female contact component being associated with an implantable medical device while the other of the male and female contact component is associated with a power source or associated cable, the male component including a plurality of male contact pins that correspond with a plurality of female contact pins of the female component;
   engaging the interfaced male and female contact so as to axially displace an urging member defined in one or both of the male and female contact component such that the urging member exerts a reaction spring force; and
   mating the male and female component in a mated position such that corresponding male and female contact pins are conductively coupled while the urging member is displaced along a longitudinal axis of the respective contact pin; and
   maintaining electrical integrity of the conductive coupling between the male and female contact pins by accommodating compliant movement of the male and female contact pins while a reaction force of the displaced urging member provides an increased contact force between corresponding male and female contact pins, wherein the urging member comprises a helical cut portion of the respective contact pin.

19. The method of claim 18, the method further comprising:
   displacing the helical cut portion of the respective contact pin by a distance sufficient to exert at least a desired contact force between conductively coupled corresponding male and female contact pins.

20. The method of claim 19, further comprising:
   wherein displacing the helical cut portion comprises matingly engaging the male and female components in a mated configuration.

21. The method of claim 18, wherein the implantable medical device is an implantable heart pump.

22. A method of manufacturing an implantable connector, the method comprising:
   defining a distal protruding surface in a distal portion of each of one or more male contact pins of a substantially cylindrical shape;
   defining a distal recessed surface in a distal portion of each of one or more corresponding female pins of a substantially cylindrical shape, wherein the distal recessed surface corresponds to a shape of the distal protruding surface in the respective one or more male contact pins;

defining a helical cut portion in a portion of the one or more male contact pins and/or the one or more female contact pins, the portion being proximal of the distal portion of the respective contact pins;

electrically coupling an electrical conductor to each of the one or more female contact pins and incorporating the one or more female pins into a female component;

electrically coupling an electrical conductor to each of the one or more male contact pins and incorporating the one or more female pins into a male component; and adapting the male and female components to interface with each other such that corresponding male and female components are conductively coupled while the helical portion of each respective male or female contact pin is displaced so as to exert a spring force in response that increases a contact force between conductively coupled contact pins.

23. The method of claim 22, further comprising:

defining a geometry of an interfacing portion of each of the male and female components to define a mated configuration in which the helical portion is displaced a sufficient distance to provide at least a desired contact force between conductively coupled contact pins.

24. An implantable connector having interfacing male and female components and adapted for use with an implantable heart pump, the connector comprising:

a plurality of contact pins disposed within the male component, each male contact pin having a proximal portion and a distal portion, the proximal portion being conductively coupled to a conductor and the distal portion having a distal engaging surface defined therein; and a plurality of female contact pins of the female component, each female contact pin having a proximal portion and a distal portion, the proximal portion being conductively coupled to a conductor and the distal portion having a distal engaging surface defined therein that is adapted for engaging with the distal engaging surface of a corresponding male contact pin of the plurality;

wherein each of the plurality of male and female contact pins are formed of a platinum-iridium alloy and include a helical cut portion defined in a region proximal of the respective distal portion, wherein the helical cut portions are configured to exert a reaction spring force in a longitudinal direction when displaced along a longitudinal axis of the respective contact pin to increase a contact force between distal engaging surfaces of the corresponding male and female contact pins when the male and female components are mated.

* * * * *

UNITED STATES PATENT AND TRADEMARK OFFICE
CERTIFICATE OF CORRECTION

PATENT NO. : 9,985,374 B2
APPLICATION NO. : 15/588470
DATED : May 29, 2018
INVENTOR(S) : William V. Hodges Page 1 of 1

It is certified that error appears in the above-identified patent and that said Letters Patent is hereby corrected as shown below:

On the Title Page

Under item (*) just below item (73), in the first column: please delete the repeated "days" after "0 days.".

In the second column, in the Abstract, item (57), Line 14: please delete "potion" and insert --portion--.

In the Claims

In Column 15, Line 56, Claim 8: please delete "one more" and insert --one or more--.

In Column 16, Line 1, Claim 13: after "wherein" insert --the--.

Signed and Sealed this
Thirteenth Day of November, 2018

Andrei Iancu
*Director of the United States Patent and Trademark Office*